United States Patent
Raffa et al.

(10) Patent No.: US 8,058,043 B2
(45) Date of Patent: Nov. 15, 2011

(54) NON INVASIVE METHOD OF ELECTROPORATION MEDIATED BY CARBON NANOTUBES AND DEVICE FOR PUTTING THE METHOD INTO PRACTICE

(75) Inventors: Vittoria Raffa, Pisa (IT); Arianna Menciassi, Pontedera (IT); Virginia Pensabene, Livorno (IT); Gianni Ciofani, Cascina (IT); Paolo Dario, Livorno (IT); Orazio Vittorio, Catania (IT)

(73) Assignee: Scuola Superiore di Studi Universitari e di Perfezionamento Sant'Anna, Pisa (IT)

( * ) Notice: Subject to any disclaimer, the term of this patent is extended or adjusted under 35 U.S.C. 154(b) by 368 days.

(21) Appl. No.: 12/515,399

(22) PCT Filed: Nov. 22, 2007

(86) PCT No.: PCT/IB2007/054754
§ 371 (c)(1),
(2), (4) Date: May 18, 2009

(87) PCT Pub. No.: WO2008/062378
PCT Pub. Date: May 29, 2008

(65) Prior Publication Data
US 2010/0035322 A1    Feb. 11, 2010

(30) Foreign Application Priority Data
Nov. 24, 2006 (IT) ................. FI2006A0295

(51) Int. Cl.
C12N 13/00 (2006.01)
C12M 1/33 (2006.01)
(52) U.S. Cl. ................. 435/173.7; 435/306.1
(58) Field of Classification Search ........... None
See application file for complete search history.

(56) References Cited

FOREIGN PATENT DOCUMENTS
DE 102004063150 7/2006
WO 2006/086672 8/2006

OTHER PUBLICATIONS

Rojas-Chapana et al (Lab Chip, 2005, 5:536-539, IDS).*
Yantzi et al (Proceedings of the IEEE International Conference on Mechatronics & Automation, Niagara Falls, Canada, Jul. 2005, p. 1872-1877, IDS).*
Tiessie et al (Biochemica et Biophysica Acta, 1984, 775:446-448).*
Phez et al (Biochemica et Biophysica Acta, 2005, 1724:248-254).*
Faurie et al (DNA and Cell Biology, 2003, 22:777-783).*
Benedict, L., et al., Static polarizabilities of single-wall carbon nanotubes, Physical Review B. 1995, 52: 8541-8549.
Rojas-Chapana, J., et al., Enhanced introduction of gold nanoparticles into vital *Acidothiobacillus ferrooxidans* by carbon nanotube-based microwave electroporation, Nano Letters 2004, 4: 985-988.
Kozinsky, B., et al., Static dielectric properties of carbon nanotubes from first principles, Physical Review Letters 2006, PRL 96: 166801-1-166801-4.
Yantzi, J.D., et al., Carbon nanotube enhanced pulsed electric field electroporation for biomedical applications, Proceedings of the IEEE International Conference on Mechatronics & Automation, Niagara Falls, Canada, Jul. 2005, 1872-1877.
Yantzi et al., "Carbon Nanotube Enhanced Pulsed Electric Field Electroporation for Biomedical Applications", pp. 1872-1877, Jul. 2005.
PCT Search Report for PCT/IB2007/054754 in the name of Scuola Superiore di Studi Universitari e Di Perfezionamento Sant'Anna filed on Nov. 22, 2007.
PCT Written Opinion for PCT/IB2007/054754 in the name of Scuola Superiore di Studi Universitari e Di Perfezionamento Sant'Anna filed on Nov. 22, 2007.

* cited by examiner

*Primary Examiner* — Laura B Goddard
(74) *Attorney, Agent, or Firm* — Steinfl & Bruno LLP

(57) ABSTRACT

A non-invasive method for the electroporation of cells contained in a substrate wherein the cells are placed in contact with carbon nanotubes and then said substrate is subjected to the action of two orthogonal pulsed electric fields generated by means of two pairs of electrodes in contact with said substrate according to a specific time sequence in such a way that, when a pair of electrodes is active, the other pair of electrodes is deactivated and vice versa. A device for performing electroporation according to this method.

21 Claims, 3 Drawing Sheets

NON INVASIVE METHOD OF ELECTROPORATION MEDIATED BY CARBON NANOTUBES AND DEVICE FOR PUTTING THE METHOD INTO PRACTICE

CROSS REFERENCE TO RELATED APPLICATIONS

The present application is the US national stage of International Application PCT/IB2007/054754 filed on Nov. 22, 2007 which, in turn, claims priority to Italian Application FI2006A000295, filed on Nov. 24, 2006.

FIELD OF THE INVENTION

The present invention relates to a non-invasive method of electroporation mediated by carbon nanotubes and a device for implementing this method.

STATE OF THE ART

As is known, electroporation is a technique used for introducing macromolecules (cellular transfection), including DNA, RNA, genes and proteins and drugs in general into cells (Neumann, E. et al., *Fundamentals of electroporative delivery of drugs and genes*, Bioelectrochem. Bioenerg. 48, 3-16, 1999) through the application of electric fields, generally pulsed, of sufficient intensity and duration for inducing a temporary increase in the permeability of the cell membrane. The high transmembrane potentials induced in this way cause the formation of minute pores (20-120 nm in diameter). The macromolecules to be introduced cross the cell membrane passing through the pores, through electrophoresis in the case of charged molecules (Neumann, E. et al., *Calcium-mediated DNA adsorption to yeast cells and kinetics of cell transformation by electroporation*, Biophys. J. 71, 868-877, 1996) or by passive diffusion in the case of neutral molecules (Neumann, E. et al., *Mechanism of electroporative dye uptake by mouse B cells*, Biophys. J. 74, 98-108, 1998).

Electroporation, as a technique which applies controlled electric fields to facilitate cell permeabilisation, was introduced in 1960 with the study of the breakdown of the cell membrane induced electrically (Coster, H. G. A., *Quantitative analysis of the voltage-current relationships of fixed charge membranes and the associated property of "punch-through"*, Biophys. J. 5: 669-686, 1965; Sale A. J. et al., *Effects of high electric fields on micro-organisms*. 1. *Killing of bacteria and yeasts*, Biochim. Biophys. Acta 148: 781-788, 1967; Sale A. J. et al., *Effects of high electric fields on micro-organisms*. 3. *Lysis of erythrocytes and protoplasts*, Biochim. Biophys. Acta 163: 3743, 1968). Neumann and colleagues were the first to demonstrate the feasibility of transfecting eukaryotic cells by electroporation (Neumann, E. et al., *Gene transfer into mouse lyoma cells by electroporation in high electric fields*, EMBO J. 1: 841-845, 1982). Initially the main application of electroporation was the transfection in vitro of animal and vegetal cells. With the development of recombinant DNA technology the technique of electroporation was widely used in vivo too (Foung, S. K. et al., *Electric field-induced cell fusion and human monoclonal antibodies*, J. Immunol. Methods 116: 117-122, 1989). More particularly pulsed electric fields were used for the release in vivo of molecules in eukaryotic cells, obtaining temporary access to the cytosol (Heller, R. et al., *Transfer of human membrane surface components by incorporating human cells into intact animal tissue by cell-tissue electrofusion in vivo*, Biochim. Biophys. Acta 1024: 185-188, 1989).

Currently, in electroporation as an in vivo technique, the pulsed electric field is generated via needle electrodes implanted in the tissue to be treated or plate electrodes applied externally in contact with the tissue. Electrodes and arrays of electrodes for the release of electrical wave forms to obtain therapeutic effects are for example described in WO 98/47562.

While the method based on the use of needle electrodes is invasive, the one based on the use of plate electrodes is non-invasive and therefore, in principle, is preferable. However it is not applicable on any part of the human body but on very limited and small portions thereof. In fact taking account, on the one hand, of the data, well known in the scientific community, on the intensity of the electric fields and the times necessary for the phenomenon of cell electroporation to take place (examples in Table 1).

TABLE 1

| Electric field $E^0$ | Frequency | Pulse duration | Number of pulses | Electrodes | Type of tissue | Reference |
|---|---|---|---|---|---|---|
| 75 V/cm | 1 Hz | 50 ms | 6 | Ring | Mouse kidney | Tsujie et al., J Am Soc Nephrol 12: 949-95 2001 |
| 100-400 V/cm | 1 Hz | 20 ms | >6 | Plate | | Mir et al., C.R. Acad. Sci. Ser. III 321: 893, 1998 |
| 200 V/cm | 1 Hz | 20 ms | 6 | Plate | Mouse muscle | Liu et al., J Gene Med, 8: 353-361, 2006 |
| 550 V/cm | 1 Hz | 100 μs | 8 | Plate | Skeletal muscle | Batiuskaite et al., Biologija, 2, 2003 |
| 750 V/cm | 1 Hz | 100 μs | 8 | Plate | Tumoral skeletal muscle | Batiuskaite et al., Biologija, 2, 2003 | and, on the other hand, of the "Guidelines for the limitation of the exposure to electric and magnetic fields that vary in time and to electromagnetic fields (up to 300 GHz)" of the International Commission for the Protection against Non-Ionising Radiation (ICNIRP), it is found that, if the threshold values given in the Guideline are observed, the depth of treatment (i.e. the distance between the plates or from the plate) could reach at most a few millimeters. This method therefore is applicable in vivo with efficacy only in areas close to the surface tissues (for example on the epidermis).

Methods of electroporation are also known that make use of "mediators", formed more particularly by carbon nanotubes (CNT).

As is known, carbon nanotubes are very thin tubular structures formed by one or more layers of graphite rolled on themselves. The carbon nanotubes, produced by arc discharge between graphite sticks, were discovered and described for the first time by Sumio Iijima ("*Helical Microtubules of Graphitic Carbon*", Nature, Vol. 354, Nov. 7, 1991, pp. 56 58). In general carbon nanotubes can be divided into two groups: single-walled nanotubes or SWNT, composed of a tubular structure formed by a layer of graphite rolled on itself and closed at the two ends by two hemispherical caps, and the multiple-walled nanotubes or MWNT, which can be considered as formed by a group of concentric SWNT nanotubes. Carbon nanotubes generally have high electrical conductivity in an axial direction, while they show a dielectric behaviour in a radial direction, are chemically stable, have high mechanical strength and a very small diameter (smaller than 100 nm) associated with a high length/diameter ratio (aspect ratio>15). For these and other properties, it has been suggested that they can play an important role in fields such as nanotechnologies, microelectronics, science of materials, biology and chemistry.

The electrical properties of a carbon nanotube are closely correlated to its geometry and its electronic configuration. In practice the CNTs, due to their high anisotropy, show very different electrical properties in an axial direction and in a radial direction. B. Kozinsky (B. Kozinsky et al., *Static Dielectric Properties of Carbon Nanotubes from First Principles*, PRL 96, 166801, 2006) characterised the static dielectric properties of SWNTs and MWNTs and provided criteria for the calculation of the radial $\in^\perp$ and axial $\in\|$ dielectric constant of single-walled nanotubes (SWNTs) and multiple-walled nanotubes (MWNTs). Simplifying, it can be summed up that all the CNTs have a dielectric radial behaviour while, axially, they are extraordinary conductors (with the exception of the armchair SWNT (m,n) with m≠3n which have a semiconductor axial behaviour).

It is also known that when a CNT is immersed in an electric field an induced dipole is generated on it and therefore a dipole moment tending to align the axis of the CNT parallel to the field (L. X. Benedict et al., Phys. Rev. B 52, 8541, 1995).

The use of CNTs as electroporation mediators has already been proposed for reducing the voltages required for irreversible electroporation in order to develop a portable lab-on-a-chip with low energy consumption (Yantzi J. D. et al., *Carbon Nanotube Enhanced Pulsed Electric Field Electroporation for Biomedical Applications*, Proceedings of the IEEE International Conference on Mechatronics & Automation Niagara Falls, Canada, 2005), or to induce the reversible permeabilisation of bacterial cells with exposure to microwaves of the cells brought into contact with the CNTs (Rojas-Chapana J. A. et al., *Enhanced Introduction of Gold Nanoparticles into Vital Acidothiobacillus ferrooxidans by Carbon Nanotube-based Microwave Electroporation*, Nano Letters, vol. 4, no. 5, pp. 985-988, 2004).

In both the cases mentioned above, which use CNTs as electroporation mediators, the behaviour of conductors in an axial direction of the CNTs is exploited, which CNTs behave as emitters of electrons. In fact, as is known, when a high electric field of the order of $10^7$ V/cm is applied on the surface of a solid with negative electrical potential, the electrons in the solid are emitted in the vacuum due to a tunnel effect. This phenomenon is known as electron field emission. High electric fields can be obtained on the tip of a very thin needle in that the electric field concentrates at the tip (tip effect). Carbon nanotubes have the following favourable properties for functioning as field emitters: 1) high aspect ratio, 2) thin tip, 3) high chemical stability and 4) high mechanical strength (Saito Y. et al., *Field emission from carbon nanotubes and its application to electron sources*, Carbon 38 169-182, 2000).

Thanks to the tip effect, the CNT require electric fields for the emission of electrons one hundred times smaller than normal conductors. However, as confirmed by all the data reported in literature, the minimum electric field threshold to be applied to a CNT for achieving the electron emission of is >$10^4$ V/cm. This energy is incompatible with the energies that can be supported by eukaryotic cells for any time exposure range and therefore intrinsically unsuitable for applications in vivo, even more so in the case wherein electroporation is performed with a non-invasive method.

The general object of the present invention is to provide a non-invasive method of electroporation, suitable for applications both in vitro and in vivo, which allows reversible cell poration without damaging the cells involved by the treatment.

A particular object of the present invention is to provide a non-invasive method of electroporation of the type mentioned above which can be implemented by electric fields of sufficiently low intensity to avoid any damage to the cells involved in the treatment.

Another particular object of the present invention is to provide a non-invasive method of electroporation of the type mentioned above which, the applied electrical voltage being equal, allows a greater penetration depth compared to the known non-invasive methods of electroporation.

Another object of the present invention is to provide a device for performing non-invasive electroporation without causing damage to the cells or tissues involved in the treatment.

SUMMARY OF THE INVENTION

These objects are achieved with the non-invasive method of electroporation and with the device for its performance according to the present invention whose basic features are disclosed in claims 1 and 13.

Essentially the non-invasive method of electroporation of a substrate containing cells according to the invention comprises the steps of bringing into contact said cells with carbon nanotubes and submitting the substrate to the action of two orthogonal pulsed electric fields generated by means of two pairs of insulated electrodes in contact with the substrate according to a time sequence determined in such a way that, when a pair of electrodes is active, the other is deactivated and vice versa.

According to a feature of the invention, the two electric fields are formed by a primary electric field with pulse duration of the between 100 µs and 50 ms and sufficient intensity for producing the cell poration and an auxiliary electric field with duration of the pulses between 10 µs and 200 µs, which has the carbon nanotubes in perpendicular alignment in relation to the primary electric field, in said time sequence the pulses of the auxiliary electric field preceding those of the primary electric field to realign the carbon nanotubes each time perpendicularly with the primary electric field.

The non-invasive electroporation device according to the invention comprises two pairs of insulated electrodes suitable for generating two pulsed electric fields oriented at 90° one in relation to the other and arranged so as to define a spatial region suitable for receiving a substrate containing cells to be porated, previously placed in contact with carbon nanotubes. Means are also provided for generating respective trains of pulses for each pair of electrodes according to a specific time sequence in which, when a pair of electrodes is active, the other is deactivated and vice versa.

Further important features of the invention are disclosed in the dependent claims.

BRIEF DESCRIPTION OF THE DRAWINGS

The features and advantages of the non-invasive method of electroporation according to the present invention and of the device for its implementation will be made apparent by the following description of an embodiment thereof, given by way of a non-limiting example with reference to the accompanying drawings, in which.

DETAILED DESCRIPTION OF THE INVENTION

Figure 1:
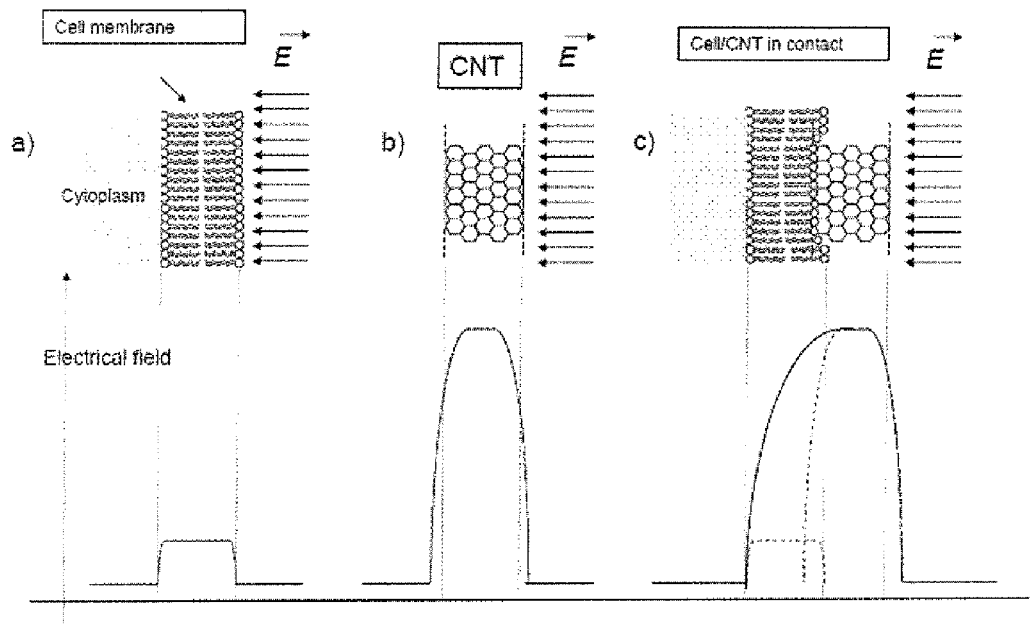
FIG. 1 shows schematically the effect of amplification of the electric field in the cell membrane at the CNT-cell contact in the method of electroporation according to the invention.

For the purpose of giving a reference terminological framework, the following is a glossary of the terms used in the description and in the claims as a basic resource of the reader.

GLOSSARY

Carbon nanotubes (CNT): any very thin tubular structure formed by one or more layers of graphite rolled on themselves, with a single wall (single-walled nanotube or SWNT), i.e. composed of a tubular structure formed by a layer of graphite rolled on itself and closed at the two ends by two semispherical caps, or with a multiple wall (multiple-walled nanotube or MWNT), that is to say comparable to a group of concentric SWNT. Any tubular structure of the type mentioned above with high electric conductivity in an axial direction and having a dielectric behaviour in a radial direction, with high, chemical stability, high mechanical strength and very small diameter (less than 100 nm) associated with a high length/diameter ratio (aspect ratio)>15.

Substrate: any material containing living cells, in particular a part of a living being (vegetable, human or animal) or a substrate separated from the living being and contained in a receptacle (for example a culture of animal, vegetable, bacterial or fungal cells).

Primary electric field: pulsed electric field effective for the purposes of electroporation.

Auxiliary electric field: pulsed electric field at right angles to the primary electric field, for aligning on each occasion the carbon nanotubes at right angles to the primary electric field.

The method of electroporation according to the invention uses carbon nanotubes (CNTs) as mediators and exploits the dielectric properties thereof.

As already mentioned, the known use of CNT as mediators of electroporation (as in Rojas-Chapana et al., 2004, cit.) is based on their axial electrical conductivity and on the consequent peak effect which allows a localised increase in the intensity of the electric field to be obtained in the point of contact between the end of the nanotube and the cell. This condition is achieved when, due to the electric field applied, the CNT orients with its axis parallel to the latter. However, as already explained, the minimum threshold of intensity of the electric field necessary for activation of the phenomenon of electrons field emission, using non-invasive techniques with plate electrodes, is too high to be supported without damage by eukaryotic cells.

According to the invention the function of electroporation mediators performed by the CNTs can also be used by exploiting their dielectric properties. This occurs when a CNT, in contact with the cell, is exposed to an electric field perpendicular to its axis. In this circumstance the intensity of the electric field in the cell membrane at the CNT-cell contact is increased by an amplification factor $\beta$, as a function of the type of CNT used and of the medium in which it is immersed, taking it to a sufficient value for causing cell poration and maintaining the intensity of the electric field applied at such a value as not to cause damage to the cells treated.

In other words and without wishing to be restricted to the theory, said $E^0$ the electric field to be applied for inducing cell electroporation in the absence of CNTs (see table 1) and $E_{CNT}^0$ the electric field to be applied in the presence of CNTs, the aforementioned amplification factor $\beta$ is such that $$E_{CNT}^0 = \frac{E^0}{\beta}$$

and it is demonstrated that it is directly proportional to the ratio between the dielectric constant $\in^m$ of the cell membrane and the radial dielectric constant $\in^\perp$ of the CNT, i.e.

$$\beta \alpha \frac{\varepsilon^m}{\varepsilon^\perp}$$

The previous formulas always hold true for CNT with aspect ratio >15.

For example, supposing that the cell membrane with which the CNTs are in contact has dielectric constant $\in^m=11.5$ (Varghese A in The Biomedical Engineering Handbook, 2nd Ed. Eds Bronzino J-D (Boca Raton: CRC Press LLC), sect. 2, chapter 11, 2000) and assuming a value of $\in^\perp$ close to 1 (Leonard F, Tersoff J, *Appl. Phys. Lett.* 81:25, 2002), the amplification factor is $$\beta \approx \frac{\varepsilon^m}{\varepsilon^\perp} \approx 10$$

FIG. 1 illustrates in quality terms the intensity of the electric field at the CNT-cell interface for a CNT attached to the cell membrane and perpendicular to the external electric field. In this figure a) represents the intensity of the electric field in the cell membrane in the presence of the applied electric field $\vec{E}$, b) represents the intensity of the electric field in the CNT in the presence of $\vec{E}$, and c) represents indicatively the amplification of the electric field in the cell membrane in contact with the CNT in the presence of $\vec{E}$.

Figure 2:
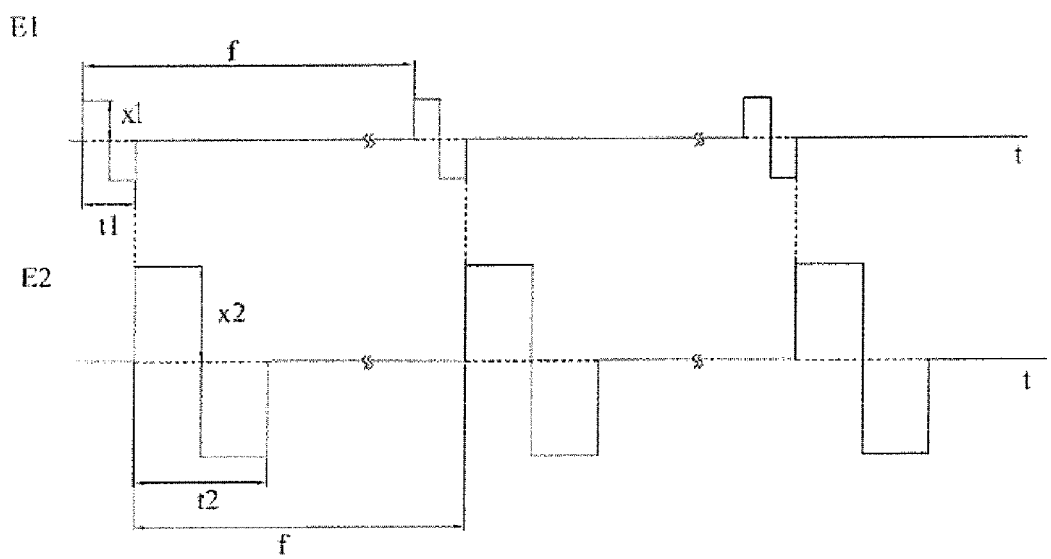
FIG. 2 shows the time sequence of application of two orthogonal pulsed electric fields in the electroporation method according to the invention.

To make sure the carbon nanotubes are at right angles to the electric field which induces cell poration, the method of non-invasive electroporation according to the invention involves subjecting a substrate containing the cells to be porated, previously brought into contact with a CNT solution, to the action of two pulsed electric fields at right angles to each other: a first pulsed electric field E2, said primary electric field, suitable for causing cell poration, and a second pulsed electric field E1, said auxiliary electric field, suitable for aligning the nanotubes in a position at right angles to the primary electric field, that is to say in the position of maximum efficacy for electroporation. The action of the two electric fields is exerted according to a time sequence in which the pulses of the two fields alternate one after the other, substantially as shown in FIG. 2, and in which the pulses of the auxiliary electric field E1 precede those of the primary electric field E2.

A possible working sequence is the following:
intensity of the auxiliary electric field E1

$$x_1 \frac{V}{cm} \text{ when } t(0, t_1)$$
$$0 \frac{V}{cm} \text{ when } t(t_1, T);$$

intensity of the primary electric field E2

$$x_2 \frac{V}{cm} \text{ when } t(t_1, t_1 + t_2)$$
$$0 \frac{V}{cm} \text{ when } t(0, t_1), (t_1 + t_2, T);$$

in which $$x_2 = \frac{E^0}{\beta} = E_{CNT}^0,$$

$x_1$, such that $0.1x_2 < x_1 < x_2$,
$t_2$, duration of the pulse of the primary electric field effective for electroporation,
$t_1$, duration of the pulse of the auxiliary electric field which produces alignment of the CNT at right angles to the primary electric field
T, period of the two wave forms.

The sequence is repeated at the frequency f=1/T and for the number n of times required by electroporation.

The time required for a nanotube to align with the applied electric field is controlled by the dipole moment which is created thereon due to the presence of the field and depends on the value of the radial dielectric constant, other features such as the viscosity of the medium and the moment of inertia being unchanged. The smaller the value of the radial dielectric constant is, the greater is the alignment time. Taking for the value of the radial dielectric constant of a nanotube the minimum, physically possible value, it is found that times longer or equal to 10 μs are sufficient for allowing alignment of the nanotube. Working values of the duration of the alignment pulse between 10 and 200 μs can be used. More particularly values between 10 and 20 μs have been found to be adequate. Time values higher than 200 μs are not advisable in that, although effective for the alignment of the CNT, they could induce cell electroporation if associated with high values of $x_1$.

Figure 4:
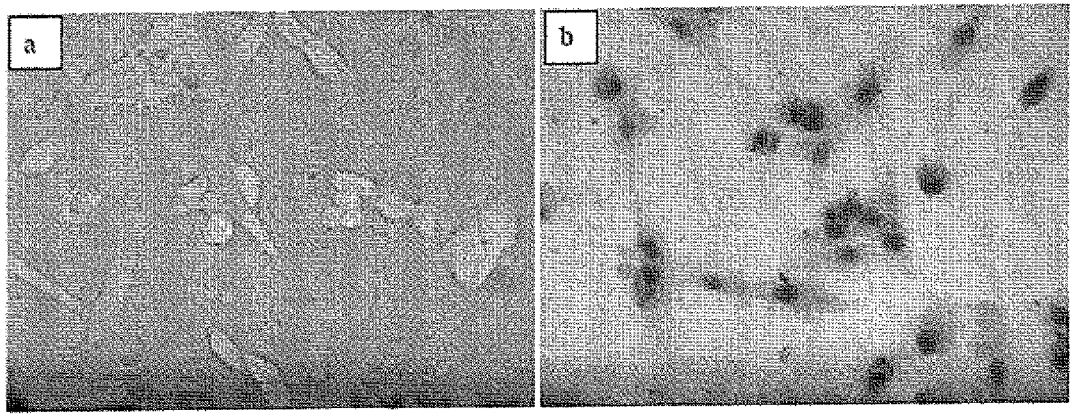
FIG. 4 shows, by way of an example, the result of application of the method according to the invention to a) CNT untreated cells, and b) to CNT treated cells, in the presence of a molecule impermeable to the cell membrane (trypan blue)

The present method is considered applicable to every, already known generic electroporation protocol already (some examples are given in Table 1), defined as number of pulses n, wave frequency f, duration of the pulse $t_2$ and intensity of the electric field $E^0$. Given a generic electroporation protocol that defines n, f and $t_2$ and $E^0$, in the present method the wave form of the primary electric field will be defined by the same values of n, f e $t_2$, with the exception of the intensity of the primary field to be applied, because $x_2$ is to be calculated as $x_2 = E^0/\beta$. By way of an example FIG. 4 shows the results of the electroporation method according to the present invention applied to the protocol supplied by Liu and colleagues (Liu et al., J Gene Med, 8: 353-361, 2006).

The values of the electroporation pulse proposed in the prior art generally vary from 100 μs to 50 ms. The electrical pulse both for the auxiliary field and for the primary field is applied biphasically so that the average time value is equal to zero. This allows the cells not to be subjected to prolonged continuous voltages and to the consequent accumulation of charge. The biphasic stimulation, commonly used for other applications, does not jeopardise the alignment of the CNT as it influences the sense and not the direction of the electric field.

The intensity of the primary electric field E2 varies according to the applications and particularly to the depth of the treatment: more particularly it may vary from 10 to 100 V/cm for surface treatments and from 100 to 750 V/cm for treatments at depth.

The frequency of the pulse, identical for the primary and auxiliary electric fields, useful for the purposes of the present invention, is between 0.1 and 1000 Hz. A preferred value of the pulse frequency is 1 Hz.

The number of successive pulses for electroporation, in accordance with what is known to the literature in the field, is between 4 and 10 and preferably between 6 and 8.

The CNT solution usable in the method according to the present invention can be prepared according to procedures known in the field, for example those described in T. Saito et al., *Chemical treatment and modification of multi-walled carbon nanotubes*, Physica B 323:280-283, 2002 (for example acid treatment and sonication in a mixture of 90% H2SO4%/60% HNO3 in a ratio of 3:1; dispersion in surface agents such as Tween 20, Pluronic F127, etc. in percentages between 0.1 and 1%; functionalisation with biomolecules such as DNA, albumin, etc.). The concentration of CNT in the electroporation solution may vary from 1 to 500 μg/ml. Preferred concentration values are between 10 and 50 μg/ml. The CNT solution can be brought into contact with the cells of the substrate in various ways according to the application, for example by simple mixing, systemic administration or injection.

Figure 3:
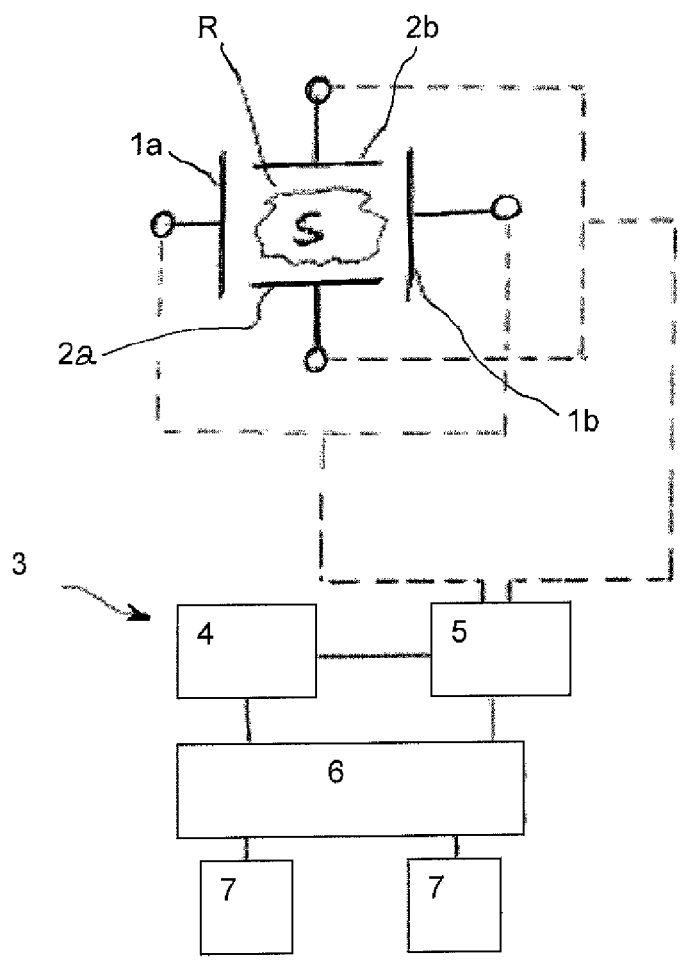
FIG. 3 shows schematically the device according to the invention.

The device which allows a CNT-mediated electroporation to be performed, in which the CNT are brought in contact with the cells oriented perpendicularly to the applied electric field is schematically shown in FIG. 3. The device is formed by two pairs of plate electrodes, denoted by 1a, 1b and 2a, 2b, covered by insulating material. The two pairs of electrodes are placed at right angles to each other to define a spatial region R intended to house a substrate S to be treated. The two pairs of electrodes are connected to a circuit 3 supplied with power from a mains or battery and comprising a pulse generator 4 adapted to release pulses of adjustable form, voltage, duration and frequency. The generator is advantageously associated with an automatic switch 5 for alternatively connecting the generator 4 to the two pairs of electrodes and is controlled by a microcontroller 6 co-operating with input-output interface unit 7, such as a keyboard and a display. The circuit 3 for the generation of pulses is substantially of a known type, such as for example described in WO 01/81533 or US 2006057706.

The first pair of plate electrodes 1a, 1b is suitable for generating the auxiliary electric field E1 which places the nanotube in a position perpendicular to the primary electric field E2 before every pulse of the latter. The second pair of plate electrodes 2a, 2b is suitable for generating the primary electric field E2 with pulse intensity and duration effective for electroporation.

As regards the dimensioning of the device according to the invention, using as an electroporation mediator a CNT solution with aspect ratio >15, the relation between the supply voltage of the electrodes for producing the primary electric field and the distance D between the electrodes is the following:

$$D = \beta \cdot \frac{V}{E^0}$$

Figure 5:
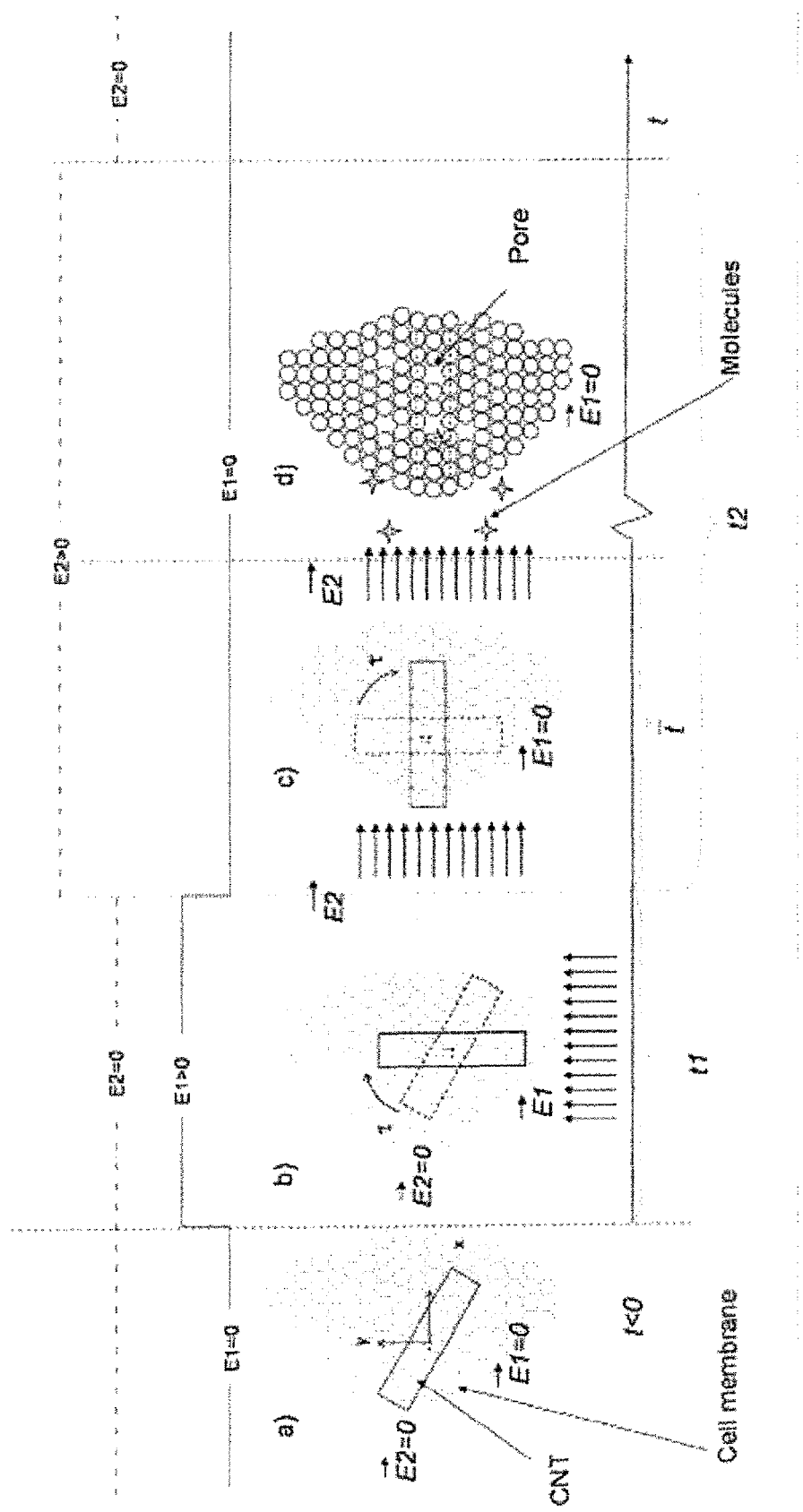
FIG. 5 shows a cell electroporation mechanism according to the present invention.

The mechanism proposed is schematically illustrated in FIG. 5:
- t<0: E1=0, E2=0. Cell and nanotube are in contact (FIG. 5, a), without an external field the CNT is generically oriented
- 0<t<t1, E1>0, E2=0. The nanotube is aligned perpendicularly to the primary electric field (FIG. 5, b)
- $t_1$<t<$t_2$ E1=>0, E2>0. Applying the primary electric field E2 the cell porates and the external molecules pass through the membrane by diffusion or electrophoresis (FIG. 5, c-d)

Example

The results of experimental tests performed on different cell lines (immortalised mouse neurons, fibroblasts of cat kidney, immortalised human neurons) show that, while without CNT the cells porate if exposed to an electric field of 200 V/cm with 6 pulses of 20 ms at the frequency of 1 Hz, in accordance with what is reported in literature (Liu et al., 2006, cit.), to electroporate the same cells with the method according to the invention with CNT a field of 35 V/cm is instead sufficient, the other conditions being the same.

The tests were performed as follows. An experimental set up was provided for performing tests in vitro composed of the following parts:
- microchip for electroporation formed by two pairs of electrodes,
- wave form generator,
- optical microscope,
- video system for image acquisition.

The microchip for electroporation consists of a double pair of electrodes coated by a thin film of transparent insulating material, made by common techniques (for example by photolithography and lift-off or through physical deposition in the vapour phase) on common substrates (plastic for cell cultures or slides for microscopy). The electrodes end with pads for connection to the external circuit. As wave form generator a Hewlett Packard model 33120 electric generator—"Arbitrary waveform generator"—was used. The cell cultures were observed by means of a Nikon TE2000U microscope equipped with a CCD NIKON DS-5MC USB2 cooled CCD videocamera.

The cells shown in FIG. 4 belong to the immortalised cell line CrFK (mouse kidney fibroblasts).

The culture was carried out according to a usual method (culture medium: Dulbecco's modified Eagle's medium with 10% of bovine foetal serum, 100 IU/ml of penicillin, 100 µg/ml of streptomycin and 2 mM L-glutamine; incubation: 37° C. in a saturated wet atmosphere containing 95% air/5% $CO_2$; passed to confluence, by trypsinization).

To perform the test approximately 5000 cells were transferred onto the microchip. The test liquid consists of:
- solution of CNTs (10 µg/ml) and Trypan blue (0.2%) in PBS (test with CNT, FIG. 4, on the right);
- solution of Trypan blue (0.2%) in PBS (test without CNTs, FIG. 4, on the left).

Trypan blue is a dye used to estimate the proportion of living cells in a culture. The reactivity of this marker is based on the fact that the chromophore is negatively charged and does not react with the cell unless there is damage to the cell membrane. The living cells (or in any case with the membrane intact) do not incorporate the dye, while those with the membrane damaged are coloured. Similarly a cell, if subjected to electroporation, should take on a blue colour in that its membrane is momentarily opened, otherwise colouring does not take place.

The carbon nanotubes solution was obtained as follows, starting from multiple-walled nanotubes (MWNT) with diameter 6-30 nm, produced by CVD (chemical vapour deposition). The MWNT were fragmented, purified and made soluble in water, using one of the methods suggested in literature (T. Saito et al., 2002, cit.). Before use the solution was sterilised with UV rays and subjected to sonication for 20 minutes.

FIG. 4 shows cells subjected to electroporation in the presence of CNT (picture b) and without CNT (picture a). This demonstrates that, when a pulse train is applied in the presence of CNT, also the cell interior is coloured by the marker, meaning that the cells have been porated. The results shown in FIG. 4 are obtained with the following test conditions: intensity of the primary electric field: 35 V/cm; intensity of the auxiliary electric field: 15 V/cm; frequency: 1 Hz; primary electric field pulses: 6; cell density: $1000/mm^2$; nanotube density: 10 µg/ml. The CNT used are: MWNT, average diameter: 14 nm; length: 1-2 µm.

Viability tests confirm that the cells electroporated according to the method of the present invention have a vitality that is always higher than 90% at 72 hours after the treatment according to the invention.

The non-invasive electroporation method according to the present invention is suitable for both in vitro and in vivo applications, and the structure of the device for putting the method into practice will vary according to the substrate on which electroporation has to be carried out. For example, if the substrate is a culture of attached cells, the two pairs of electrodes in FIG. 3 can be thin films deposited directly on the cell culture dish. The thin film can be an adhesion layer (for example Cr, Ti, 50 nm in thickness), a conductor layer (for example Au, 300 nm in thickness) and an insulating layer (for example $SiO_2$, 35 nm in thickness). If the substrate is a culture of suspended cells, a standard cuvette for spectrophotometry can be modified, by inserting the two pairs of electrodes at the vertical walls of the internal surface of the cuvette. Each electrode can consist of a metal strip (for example Cu, Al, 200 µm in thickness) insulated with a thin film (for example biocompatible glue or thin adhesive tape, 10 µm in thickness).

If electroporation is to involve a part of the human or animal body, the two pairs of electrodes will be shaped so as to be arranged around said part so that the electric fields generated by them are at right angles one to the other. Advantageously the two pairs of electrodes may be supported by an insulating band, or incorporated therein, having a size suitable for application around the body part to be treated.

The non-invasive method of electroporation according to the present invention may be used both for study and research purposes and for therapeutic purposes. Through this method bioactive molecules in general, nucleic acids and genetic material, proteins, substances with pharmacological properties and chemotherapy substances, neuroregenerators, etc. can be introduced in target cells, if necessary also using nanotubes functionalised with substances or molecules of the above type.

An important advantage of the method of electroporation according to the present invention consists in the fact that, thanks to the low voltages applied and to the fact that the treatment is localised, the only cells treated with CNTs being those effectively involved by the electroporation, undesirable effects are not caused on the surrounding tissues, unlike what may occur with the known methods of electroporation. The method of the present invention may also be applied to perform cell lysis (or destruction). In this case the working sequence may be the following:

intensity of the auxiliary electric field E1

$$x_1 \frac{V}{cm} \text{ for } t(0, t_1)$$
$$0 \frac{V}{cm} \text{ for } t(t_1, T);$$

intensity of the primary electric field E2

$$1.5 \cdot x_2 \ldots 5 \cdot x_2 \frac{V}{cm} \text{ per } t(t_1, t_1 + t_2)$$
$$0 \frac{V}{cm} \text{ for } t(0, t_1), (t_1 + t_2, T);$$

where the meaning of the symbols is as defined and what is not specified remains unchanged. By applying these electric fields the effect is the destruction of the cells in contact with the CNT, without any damage to the cells not treated with the CNTs. This method of selective cell destruction can be advantageously applied in cell therapy, for example in the treatment of cancer.

Variations and/or modifications may be made to the non-invasive method of electroporation and to the relevant device according to the present invention without departing from the scope of the invention, as set forth in the following claims.

The invention claimed is:

1. A non-invasive method for electroporation of cells contained in a substrate, comprising
placing the cells in contact with carbon nanotubes;
subjecting said substrate to action of two orthogonal pulsed electric fields generated by two pairs of insulated electrodes in contact with said substrate according to a specific time sequence in such a way that, when a pair of electrodes is active, the other pair of electrodes is deactivated and vice versa.

2. The method of electroporation according to claim 1, wherein the two orthogonal pulsed electric fields are formed by a primary electric field with pulses of duration of between 100 μs and 50 ms and an intensity sufficient for producing cell poration, and an auxiliary electric field with pulses of duration between 10 μs and 200 μs, the auxiliary electric field placing the carbon nanotubes in perpendicular alignment in relation to the primary electric field.

3. The method of electroporation according to claim 2, wherein the pulses of the auxiliary electric field precede the pulses of the primary electric field to realign, after every pulse of the primary electric field, the carbon nanotubes at right angles to the primary electric field.

4. The method according to claim 2, wherein intensity of the auxiliary electric field is between 0.1 and 1 times an intensity of the primary electric field.

5. The method according to claim 2, wherein intensity of the primary electric field is between 10 and 1000 V/cm.

6. The method according to claim 1, wherein pulse frequency of the pulsed electric fields pulses is between 0.1 and 1000 Hz.

7. The method according to claim 6, wherein the pulse frequency is 1 Hz.

8. The method according to claim 1, wherein pulses generated by the pulsed electric fields are in a number of between 4 and 10.

9. The method according to claim 8, wherein the number of the pulses is between 6 and 8.

10. The method according to any one of the previous claims, wherein the carbon nanotubes are in a solution having a concentration between 1 and 500 μg/ml.

11. The method according to claim 10, wherein the concentration of the solution of carbon nanotubes is between 10 and 50 μg/ml.

12. The method according to claim 1, wherein placing the cells in contact with the carbon nanotubes occurs through direct mixing, systemic administration, or injection.

13. An electroporation device for non-invasive electroporation through carbon nanotubes, comprising
two pairs of electrodes for generating two pulsed electric fields oriented at 90° with respect to one another and arranged to define a spatial region suitable for receiving a substrate containing cells to be porated, the cells placed in contact with the carbon nanotubes, and
means for generating respective trains of pulses for each pair of electrodes according to a specific time sequence wherein, when a pair of electrodes is active, the other pair is deactivated.

14. The electroporation device according to claim 13, wherein the two electric fields are constituted by
a primary electric field with pulses of duration between 100 μs and 50 ms and an intensity sufficient for producing cell poration and
an auxiliary electric field with pulses of duration between 10 and 200 μs, the auxiliary electric field adapted to arrange the carbon nanotubes in perpendicular alignment in relation to the primary electric field.

15. The electroporation device according to claim 14, wherein the pulses of the auxiliary electric field precede the pulses of the primary electric field to realign after every pulse of the primary electric field the carbon nanotubes at right angles to the primary electric field.

16. The electroporation device according to claim 14, wherein intensity of the auxiliary electric field is between 0.1 and 1 times an intensity of the primary electric field.

17. The electroporation device according to claim 14, wherein the intensity of the primary electric field is between 10 and 1000 V/cm.

18. The electroporation device according to claim 13, wherein pulse frequency of the pulsed electric fields is between 0.1 and 1000 Hz.

19. The electroporation device according to claim 18, wherein the pulse frequency is 1 Hz.

20. The electroporation device according to claim 13, wherein pulses generated by the pulsed electric fields are in a number of between 4 and 10.

21. The electroporation device according to claim 20, wherein the number of pulses is between 6 and 8.

* * * * *